United States Patent [19]

McDougall

[11] Patent Number: 5,617,601
[45] Date of Patent: Apr. 8, 1997

[54] BRUSHES FOR PERSONAL HYGIENE PURPOSES

[76] Inventor: Gregory J. McDougall, 1008, Telford Gardens, Kowloon Bay, Kowloon, Hong Kong

[21] Appl. No.: 318,980

[22] Filed: Oct. 6, 1994

[30] Foreign Application Priority Data

Oct. 8, 1993 [GB] United Kingdom .................. 9320751

[51] Int. Cl.⁶ ........................... A61C 17/34; A46B 13/02
[52] U.S. Cl. ................................. 15/22.1; 15/28
[58] Field of Search ..................... 15/22.1, 22.2, 15/22.4, 23, 24, 28, 29

[56] References Cited

U.S. PATENT DOCUMENTS

| | | |
|---|---|---|
| 2,598,275 | 5/1952 | Lakin . |
| 3,181,189 | 5/1965 | Leyden .................. 15/22.1 |
| 4,827,550 | 5/1989 | Graham et al. ........... 15/22.1 |
| 4,845,795 | 7/1989 | Crawford et al. ......... 15/22.1 |
| 4,991,249 | 2/1991 | Suroff .................... 15/22.1 |
| 5,000,684 | 3/1991 | Odrich ................... 15/22.1 |
| 5,068,939 | 12/1991 | Holland .................. 15/22.1 |
| 5,072,482 | 12/1991 | Bojar et al. .............. 15/180 |
| 5,077,855 | 1/1992 | Ambasz .................. 15/22.2 |
| 5,088,145 | 2/1992 | Whitefield ............... 15/22.2 |
| 5,177,826 | 1/1993 | Vrignaud ................ 15/22.1 |
| 5,213,434 | 5/1993 | Hahn ..................... 403/59 |
| 5,226,206 | 7/1993 | Davidovitz et al. ........ 15/22.1 |
| 5,359,747 | 11/1994 | Amakasu ................ 15/22.1 |

FOREIGN PATENT DOCUMENTS

| | | | |
|---|---|---|---|
| 4003305 | 8/1991 | Germany ............... 15/22.1 |
| 477799 | 1/1938 | United Kingdom ....... 15/28 |
| 0500517 | 2/1939 | United Kingdom . |
| 1583558 | 8/1977 | United Kingdom . |
| 91-13570 | 9/1991 | WIPO . |
| 93-10721 | 6/1993 | WIPO . |

*Primary Examiner*—Mark Spisich
*Attorney, Agent, or Firm*—Blakely, Sokoloff, Taylor & Zafman

[57] ABSTRACT

A toothbrush is disclosed which comprises a rotatably mounted toothbrush head, 100, a connection member, 150, for connection to a linear reciprocal drive means contained in hand-held casing and a flexible member, 160, formed preferably from steel wire or ribbon disposed between the connection member, 150, and the head, 100, and for converting linear reciprocal motion of the connection member to rotational motion of the head.

22 Claims, 5 Drawing Sheets

BRUSHES FOR PERSONAL HYGIENE PURPOSES

FIELD OF THE INVENTION

This invention relates to a brush for personal hygiene purposes more particularly, but not exclusively, to a toothbrush.

DISCUSSION OF THE PRIOR ART

Power driven toothbrushes, for example, electric toothbrushes, have been proposed in which either a toothbrush head or the bristles protruding therefrom are driven to move in a reciprocally rotational manner.

It is a disadvantage of the such proposed toothbrushes that the transmission from a power means to the toothbrush head to drive this in reciprocal motion is generally complicated and thus expensive to manufacture.

It is the object of the invention to provide an improved powerable brush for personal hygiene purposes.

SUMMARY OF THE INVENTION

According to the invention in the first aspect, there is provided a brush for personal hygiene purposes comprising a rotatably mounted brush head, a connection member for connection to a linear reciprocal drive means and a flexible member disposed between the connection member and the head and for converting linear reciprocal motion of the connection member to rotational motion of the head. With an arrangement of this type, complicated gearing arrangements for converting the reciprocal motion of the connection member to rotational movement of the brush head are not needed, thus simplifying the construction of the brush.

Preferably the flexible member is formed from metal wire and is biased in a direction away from the direction of linear reciprocal motion of the connection member.

In a further preferred form, the flexible member is provided with a loop which is arranged to move in reciprocation with the connection member in a channel, the edges of the loop contacting the sides of the channel to support that portion of the flexible member.

According to the second aspect, the invention provides a brush for personal hygiene purposes comprising a brush for personal hygiene purposes comprising: a main body; a detachable head part having a rotatably mounted brush head; a driven member connected to a linear reciprocal drive means in said main body; a connecting member connected to the brush head to transmit reciprocal drive to the brush head; and coupling means provided on said driven member and on said connecting member to provide a releasable coupling therebetween, said coupling means being adapted to provide coupling between said members, when the head part is in a first orientation relative to the main body part, and to allow said members to be detached when in a second orientation in which said head part is rotated relative to the main body.

By this means a simple rotation of the head part is sufficient to couple or uncouple the driven and connecting member.

Preferably, the main body and head part are provided with engagement means to allow these to be push-fitted together or pulled apart when the head part is in the first orientation, and when fitted, rotated to the second orientation in which the head part is prevented from release. This construction means that the coupling between driven and connecting members is effected as the head part is fitted onto the main body.

In a preferred embodiment, the coupling means comprise a pair of opposed legs extending from an end of the connecting member having inwardly directed fingers, and a pair of grooves formed in opposite sides of the driven member within which the fingers are engagable when the head part is in the second orientation. The engagement means comprise an axial plug formed on the main body, for receipt in a socket-like end of the head part, the plug being formed with at least one outwardly directed locking lug, and the head part being formed with a lug-receiving groove having an axial portion to allow a push-fit of the head part onto the housing, and a circumferential portion defining internally a shoulder behind which the lug engages on rotation of the head part to the second orientation. One of the driven member and connecting member is formed at its coupling end with a locating pin, the other having a locating socket. The locating pin is at the end of the driven member, which narrows towards the pin, whereby the opposed legs are pushed apart as the driven member and connecting member are coupled together.

In a further aspect, the invention provides means for moving the connection member reciprocally comprising drive means for driving a cam, the cam comprising a circular member offset relative to a driving axis, the circular member being held for rotation relative to a follower connectable to the connection member via a linear guide. Rotation of the offset circular member causes a combined pivotal and linear reciprocal movement of the follower, with only the linear reciprocal component being transferred to the guide.

BRIEF DESCRIPTION OF THE DRAWINGS

Embodiments of the invention will now be described, by way of example, with reference to the accompanying drawings in which;

FIG. 9(*a*) is an exterior view of a toothbrush;

FIG. 9(*b*) is a part-sectional view to show the coupling between a driven member and connecting member.

DESCRIPTION OF THE PREFERRED EMBODIMENTS

Figure 1:
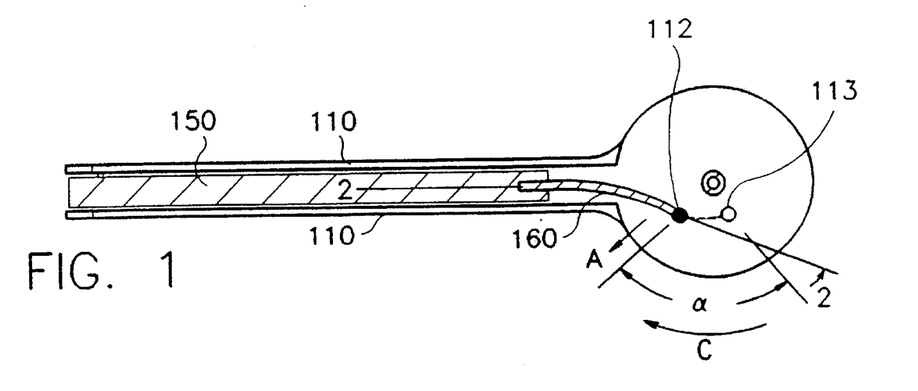
FIG. 1 is a sectioned plan view of the transmission elements of a first embodiment of the invention.
Figure 2:
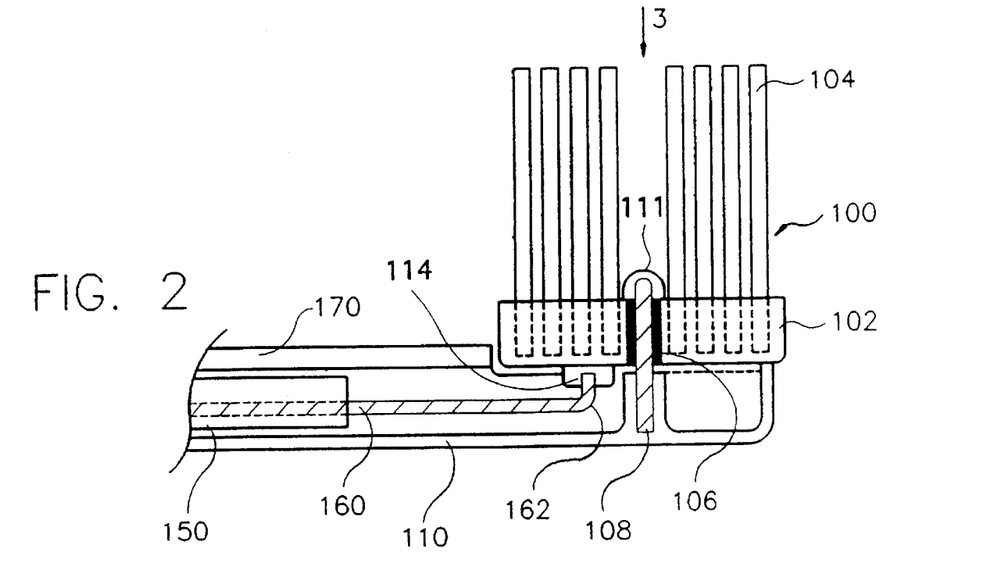
FIG. 2 is a sectional side view across 2—2 of FIG. 1 showing, in addition, a brush head of the embodiment of the invention.
Figure 3:
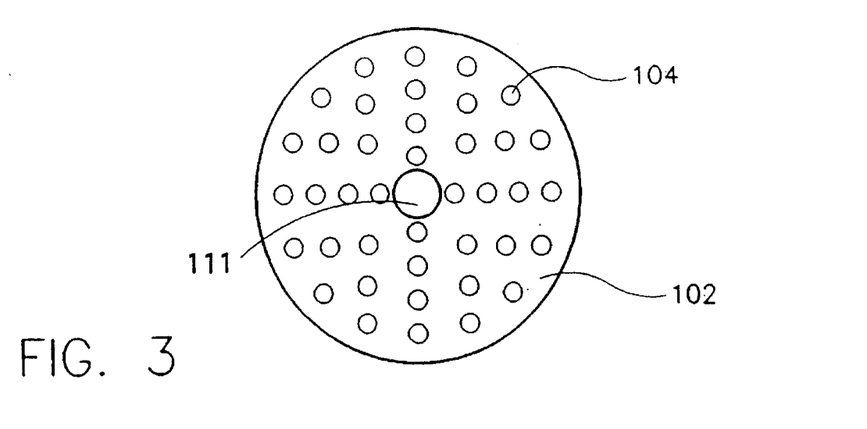
FIG. 3 is a view in the direction of arrow 3 of FIG. 2 of the brush head.

With reference to the FIGS. 1–3, an embodiment of a brush, in this case a toothbrush, is shown. The toothbrush is arranged to be power driven in a rotationally reciprocal manner and comprises a head, 100, having a rotatable base member, 102, from which an array of bristles, 104, project as shown more clearly in FIGS. 2 and 3. The member, 102, is provided with an axially disposed bore, 106, through which a mounting pin, 108, projects.

The pin, 108, is connected at one end to base member, 110, and the head, 100, is held in place for free rotation on the pin by means of a cap, 111.

The base member, 110, forms a channel in which a connection member, 150, for connection to a reciprocal driving means (shown in FIGS. 4 and 5) is provided. The connection member 150 is connected to member 102 of head 100 by means of a flexible member, 160, formed preferably from spring steel wire or ribbon. The flexible member, 160, is attached to the connection member, 150, by means of adhesive or a mechanical fitting and includes an upstanding free end, 162, which engages a corresponding bore, 114, which is disposed in member 102 radially outwardly of the centre.

By moving the member 150 between the positions shown by full lines (112) and by phantom lines, (113) in FIG. 1, the flexible member will place a torque on head, 100, thus causing this to rotate. If the member, 150, is moved reciprocally, the head will rotate backwards and forwards through an angle α, (in this case, 120°) between positions defined by the different relative positions of the end 162 that is between positions 112 and 113. The member, 160, is flexible but sufficiently rigid to rotate the head, 100, in response to force supplied from member 150, and at the same time, conform to the rotated position of opening 114.

The member, 160, does not have a linear neutral position but is biased in the direction of arrow A, ie it is bent so as to exert a force in the direction of the arrow A in a direction generally perpendicular to the direction of movement. Such an arrangement acts to prevent the member, 160, when in position 112 accidentally going "over-centre" and continuing a clockwise stroke in the direction of arrow C, rather than reciprocating in an anti-clockwise direction back to position 113.

The member, 110, provides a base and upstanding sides to form a channel in which member 150 reciprocates, and a cover, 170, is affixed to the sides of member 110 to encase the member, 150.

Figure 4:
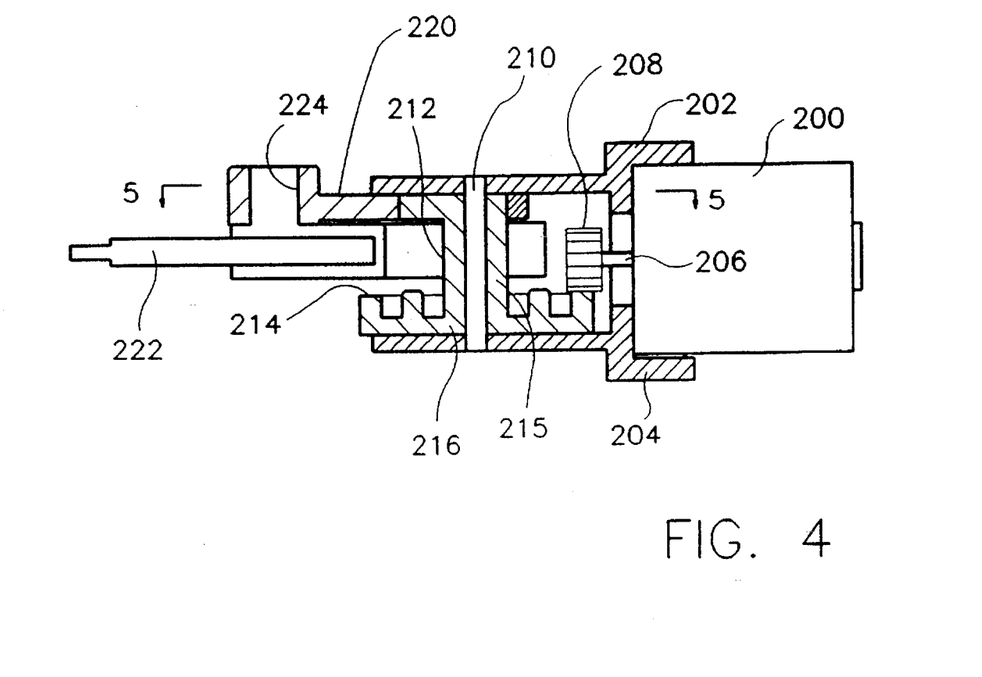
FIG. 4 is a sectional side view of a reciprocating drive mechanism of the embodiment of the invention with FIG. 5 being a view in the plane 5—5 of FIG. 4.
Figure 5:
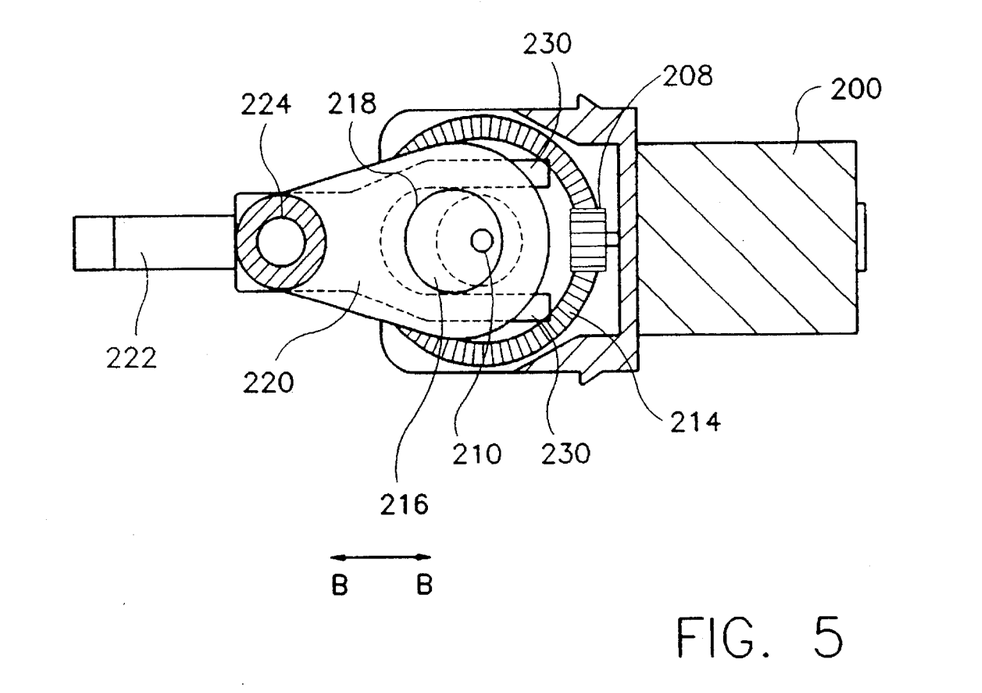

The free end of member 150 is provided with means for connection to a driving member, 222, when the brush is attached to a driving means (illustrated in FIGS. 4 and 5). Such a driving means is preferably contained within a hand-held casing in a manner of a conventional electric toothbrush, and which will be described further below. Member 110 is connected by known means to the casing so that member 110 provides a support integral with the toothbrush casing while allowing member 150 to be driven reciprocally by the driving means.

With reference to FIGS. 4 and 5, a driving means for the toothbrush, shown in FIGS. 1–3, is shown which comprises a motor, 200, to which two supporting members, 202, 204 are connected. Motor, 200, includes a shaft, 206, connected to a pinion gear, 208. A support shaft, 210, is connected between supporting members, 202, 204 and rotatably supports a driven member, 212, which includes, at one end, an annular rack, 214, for engagement with pinion, 208, and at the other, a circular member, 216, connected to the rack, 214, by a cylindrical portion, 215. The circular member, 216, is offset relative to shaft 210, as shown more clearly in FIG. 5, and is held in a corresponding opening, 218, in a follower, 220, the member 216 and follower 220 being relatively rotatable. Follower 220 is connected to a drive member, 222, by means of a pivot joint, 224.

In use, rotation of motor, 200, will drive pinion gear, 208, which will in turn cause rack, 214, to rotate correspondingly, thus rotating member 212. As circular member, 216, is offset, this will follow an eccentric motion which will cause follower 220 to follow the same path of motion, thus moving pivotally about bearing 224, but also moving reciprocally in the direction of arrows B-B of FIG. 5, and causing drive member 222 to follow such motion.

Drive member 222 further includes first and second legs, 230, which mate against the side of the central cylindrical portion, 215, of driven member, 212, which acts to guide the member 222 on a linear path.

Figure 6:
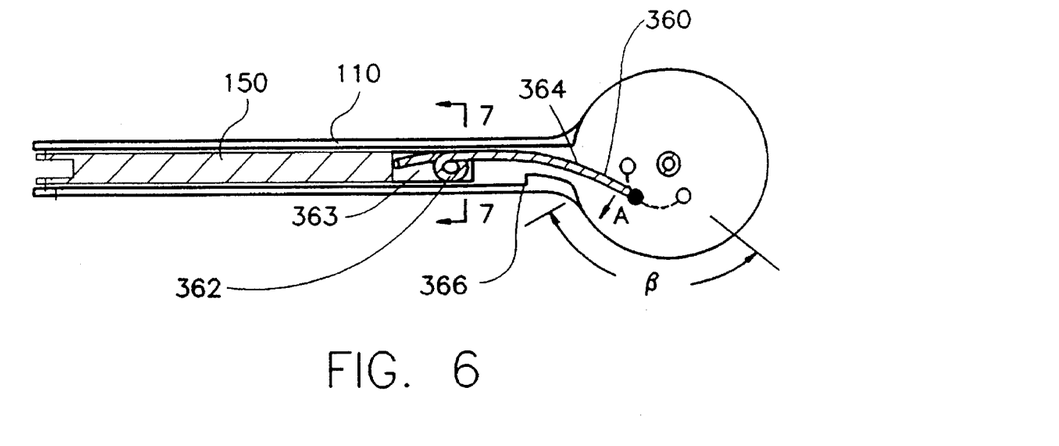
FIG. 6 is a view similar to FIG. 1 illustrating a second embodiment of the invention.
Figure 7:
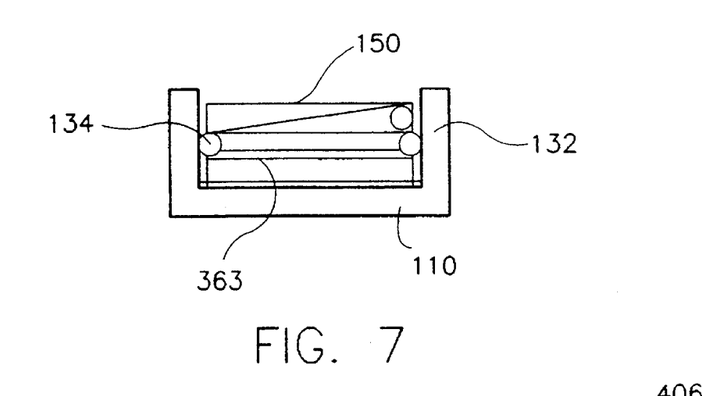
FIG. 7 is a view in the direction 7—7 of FIG. 6.

A further embodiment of the invention is illustrated in FIGS. 6 and 7. FIG. 6 is similar to FIG. 1 with the main difference being that the flexible member (here given reference 360), includes a loop, 362, disposed between the connections to member 150 and head, 100 and resting on a shelf, 363, of member, 150. The loop, 362 has two functions. The first is that the edges of the loop are arranged to touch the sides 132, 134, of support member 110, thus steadying the flexible member as a whole. Secondly, the loop adds rigidity to the connection to the member 150, with the flexible function being provided by the portion of the member, 364, between the loop and the head, 100, which is biased in the direction of arrow A. With such an arrangement, the angle of rotation of the head can be increased to angle β (120°), to just before the path of reciprocation of the member 150.

A stop, 366, is also provided which limits the movement of the connection member, 150. This allows easy engagement of the connection member with the drive member, 222, when the two are pressed together without damage to the flexible member and head.

Figure 8:
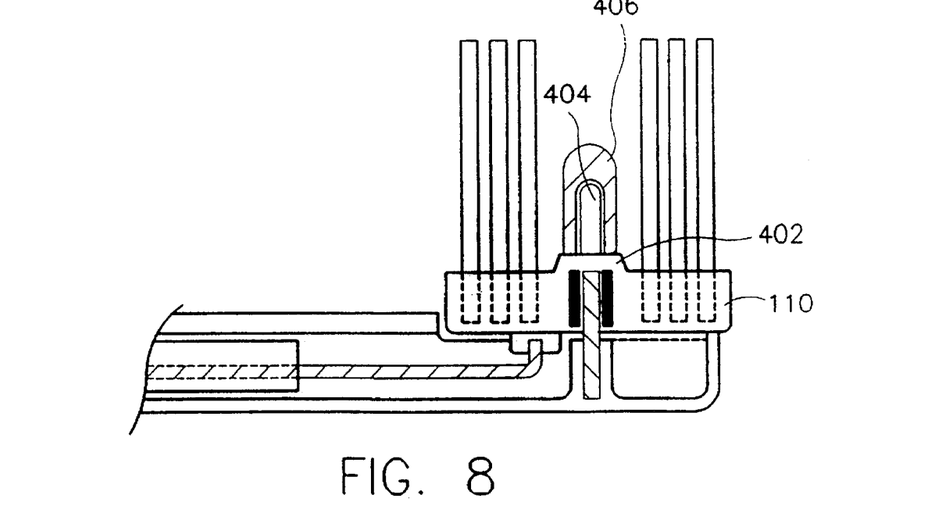
FIG. 8 is a sectional view showing the brush head in accordance with a second embodiment of the invention.

In an alternative arrangement of the head illustrated in FIG. 8, a central portion of the base is provided with an upstanding disc-like portion 402 with a central pin 404.

This central pin 404 is covered by a cap 406 formed of a soft resilient plastics or rubber-like material. The cap is arranged to lie a distance below the level of the bristles. This structure serves to limit the pressure with which the head is pressed against the teeth; if the user presses the head too hard against the teeth, he will feel the cap 406. This has the advantage that it reduces the chances of damage to the user's teeth and gums from the bristles, and also reduced damage and wear of the bristles, extending brush head life.

Figure 9A:
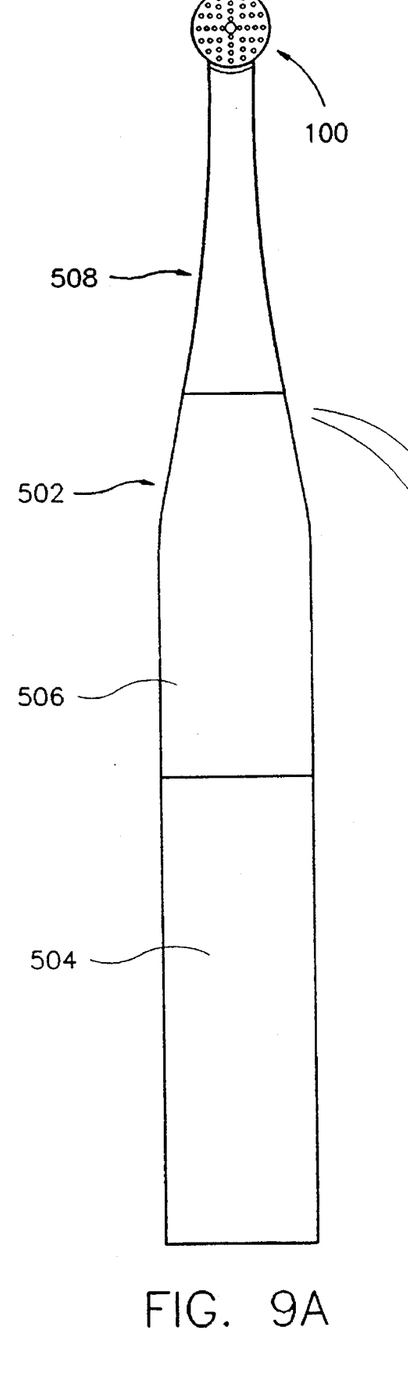

FIG. 9(a) shows the exterior of the entire toothbrush which has a main body 502, including a lower casing part 504 which houses a recharging unit, and fixed thereto a motor casing part 506 which houses the driving means and motor 200 described above. Detachably connected to the body 502 is the brush part 508 which has the rotatable head 100 at its end. The brush part 508 includes the member 110 and connecting member 150 described above.

Figure 10:
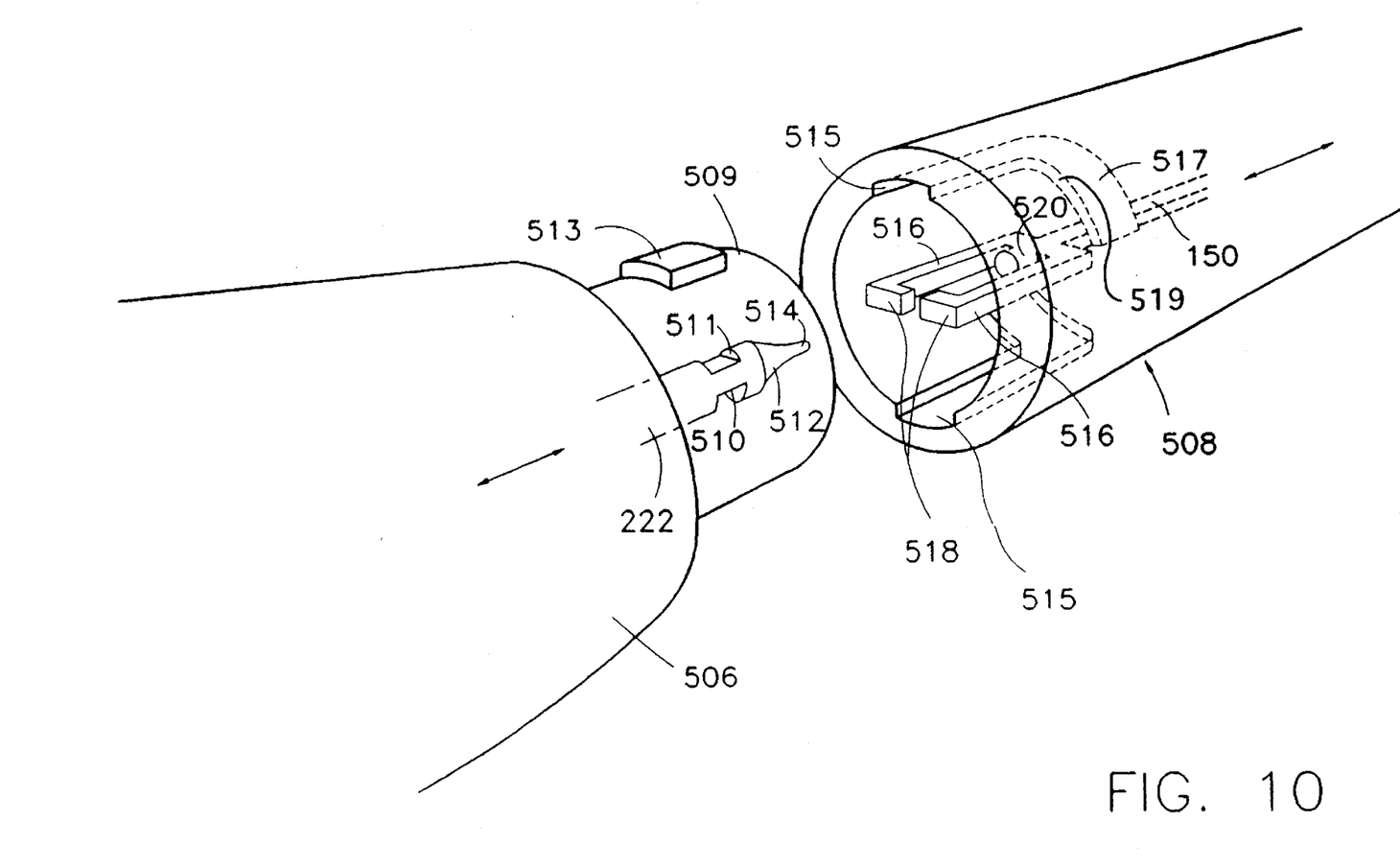
FIG. 10 is a detailed view showing the coupling between driven member and connecting member, and between housing parts.

As can be seen in FIG. 10, means are provided on the main body 502 to allow releasable attachment of the brush part 508. These comprise a plug part 509 formed on the end of the casing part 506 which push-fit within a lower opening of the brush part 508. The plug part 509 is formed with a pair of lugs 513 which fit in grooves 515 in the brush part. The lugs 513 and grooves 515 are relatively disposed so that after the brush part 508 has been push-fitted onto the casing part 506, it must then be rotated through a quarter turn to bring these into appropriate alignment. During this rotation, the lugs 513 move in internal grooves 517, engaging behind shoulder 519 so that the brush part 508 cannot be pulled off the casing part 506. It is preferably arranged that the lugs 513 are of different width to each other, so that the brush part can only be fitted in a single orientation.

Figure 9B:
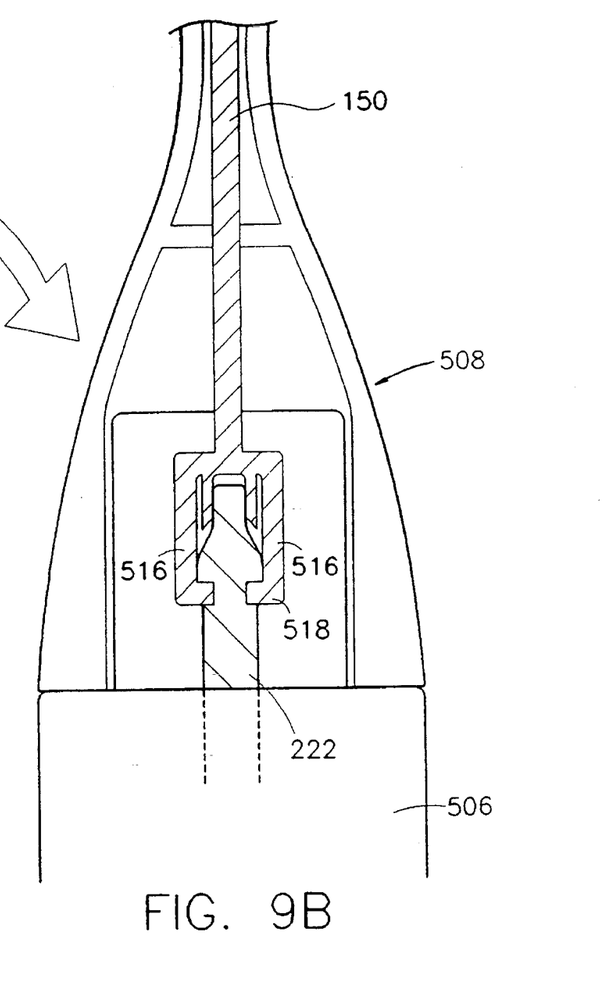

As can be seen in FIGS. 9(b) and 10, means are provided to allow the connecting member 150 to be coupled to the driving member 222 as the brush part 508 is fitted on the main body 502, and to be uncoupled on detachment of the brush part. In particular, the driving member 222 is formed with a pair of cut-outs or grooves 510, on opposite sides thereof, which define shoulders 511 at a forward end thereof. The forward or insertion end of the driving member 222 is formed with a conical portion 512 and a locating pin 514.

The coupling end of the connecting member 150 is formed with a pair of opposed legs 516 formed of a resilient material such as springy plastics or metal which have inwardly directed fingers 518. Formed centrally on the connecting member 150 is a locating socket 520.

On attachment of the brush part 508, as this is pushed onto the end of the body 502, the legs 516 will become splayed apart as they move over the portion 512 and onto the regions of the driving member 222 between the grooves 510. Then, as the brush part 508 is rotated, to lock this onto the body 502, the fingers 518 will engage in the groves 510 so that the members 222 and 150 are coupled for linear reciprocal motion. The locating pin and socket assist in accurate coupling.

On detachment, as the brush part 508 is rotated, the fingers will move apart as they move from the grooves 510 to the adjacent portion on the connecting member. The brush part 508 can then simply be pulled from the casing 506.

It will be appreciated that because the driving member 222 is reciprocally driven, it may stop at a range of positions relative to the casing part 506 and socket 520. The position of FIG. 10 corresponds to a position in which the driving member 222 is close to its forward-most position. Similarly, the connecting member 150 may be at a variety of positions relative to its housing. If the driving member 222 is in an extended position, and the connecting member 150 also in an extended position (away from the head), then on attachment the connecting member 150 will be pushed towards the head by the member 222 (which will not move) and the head will rotate very slightly. If the driving member 222 is in a retracted position, then as the brush part 508 is push-fitted on the casing part 506, the fingers 518 will not reach the region of the driving member 222 between the grooves 510. However, when the motor is activated, the fingers will then snap-fit into the grooves 510 on the first forward stroke of the driving member 222. This arrangement can thereby provide reliable coupling of the drive, irrespective of the positions of the driving member 222 and connecting member 150.

It will be appreciated that the locations of the coupling means could be reversed between the driven member 222 and connecting member 150. Similarly, the positions of locating pin 514 and socket 520 could be reversed.

I claim:

1. A brush for personal hygiene purposes comprising an elongated housing, a rotatably mounted brush head supported on the housing, a connection member for connection to a linear reciprocal drive means providing drive in a direction generally parallel to the length of the housing, and a flexible member connected between the connection member and the head for converting linear reciprocal motion of the connection member to rotational motion of the head, the flexible member being biased in a direction away from the direction of the linear reciprocal motion of the connection member.

2. A brush as claimed in claim 1 where in the flexible member is formed form metal wire.

3. A brush as in claim 1 wherein the flexible member is made of a material selected from the group consisting of wire and ribbon.

4. A brush as claimed in claim 1 wherein the housing includes a channel in which the connection member reciprocates.

5. A brush as claimed in claim 1 wherein the flexible member is bent to form a loop therein.

6. A brush as claimed in claim 5 wherein the housing includes a channel therein having sides, in which the flexible member reciprocates, and wherein the loop contacts the sides of the channel.

7. A brush as claimed in claim 1 further comprising a stop for limiting movement of the connection member.

8. A brush as claimed in claim 1 wherein the brush head comprises a circular base upon which a plurality of bristles project, the base having first means for receiving a pivot and second radially offset means for receiving an end of the flexible member.

9. A brush as claimed in claim 1 wherein the linear reciprocal drive means includes drive means for driving a cam, the cam comprising a circular member offset relative to a driving axis, the circular member being held for rotation in a follower connectable to the connection member.

10. A brush as claimed in claim 9 wherein the circular member is connected to an annular rack engagable by a gear connected to the drive means.

11. A brush as claimed in claim 9 wherein the follower is connected to a linearly guided member via a pivot, the linearly guided member being connectable to the connection member.

12. A brush as claimed in claim 1, being a powered toothbrush.

13. A brush as claimed in claim 8 wherein the base is provided with a central upstanding protrusion having a free end which lies below ends of the bristles.

14. A brush as claimed in claim 13 wherein the central upstanding protrusion is at least partly formed of a soft resilient material that limits pressure with which the brush head brushes against a surface.

15. A brush for personal hygiene purposes comprising:
a main body;
a detachable head part operably connected to said main body, having a rotatably mounted brush head;
a driven member connected to a linear reciprocal drive means in said main body;
a connecting member connected to the brush head to transmit reciprocal drive to the brush head; and
coupling means provided on said driven member, and on said connecting member to provide a releasable coupling therebetween, comprising a pair of freely extending opposed legs extending from an end of one of the connecting member and driven member, said legs having inwardly directed fingers, and a pair of grooves formed in opposite sides of the other of the connecting member and driven member within which the fingers are engageable when the head part is in a first orientation relative to the main body, the coupling means being adapted to allow said members to be detached when in a second orientation in which said head part is rotated relative to the main body.

16. A brush as claimed in claim 15 wherein the tip of the driven member includes a tapering surface narrowing towards the end of the tip which serves to urge the legs apart on coupling.

17. A brush as claimed in claim 16 wherein the tapering surface is conical.

18. A brush as claimed in claim 15 wherein the main body and head part are provided with engagement means to allow these to be push-fitted together or pulled apart when the head part is in second orientation, and when fitted, rotated to the first orientation in which the head part is prevented from release.

19. A brush as claimed in claim 18 wherein the engagement means comprise an axial plug formed on the main body, for receipt in a socket-like end of the head part, the plug being formed with at least one outwardly directed locking lug, and the head part being formed with a lug-receiving groove having an axial portion to allow a push-fit of the head part onto the main body, and a circumferential portion defining internally a shoulder behind which the lug engages on rotation of the head part to the first orientation.

20. A brush as claimed in claim 15 wherein one of the driven member and connecting member is formed at its coupling end with a locating pin, the other having a locating socket.

21. A brush for personal hygiene purposes comprising:

a main body;

a detachable head part operably connected to said main body, having a rotatably mounted brush head;

a driven member connected to a linear reciprocal drive means in said main body;

a connecting member connected to the brush head to transmit reciprocal drive to the brush head;

coupling means provided on said driven member and on said connecting member to provide a releasable coupling therebetween, said coupling means being adapted to provide coupling between said members when the head part is in a first orientation relative to the main body part and to allow said members to be detached when in a second orientation in which said head part is rotated relative to the main body;

engagement means comprising an axial plug formed on the main body, for receipt in a pocket like end of the head part, the plug being formed with at least one outwardly directed locking lug, and the head part being formed with a lug-receiving groove having an axial portion to allow a push-fit of the head part onto the main body, and a circumferential portion defining internally a shoulder behind which the lug engages on rotation of the head part to the first orientation in which the head part is prevented from axial release.

22. A brush for personal hygiene purposes comprising:

main body;

detachable head part operably connected to said main body, having a rotatably mounted brush head;

a driven member connected to a linear reciprocal drive means in said main body;

a connecting member connected to the brush head to transmit reciprocal drive to the brush head;

coupling means provided on said driven member and on said connecting member to provide a releasable coupling therebetween, said coupling means being adapted to provide coupling between said members when the head part is in a first orientation relative to the main body part and to allow the said members to be detached when in a second orientation in which said head part is rotated relative to the main body;

one of the driven member and connecting member being formed at its coupling end with a tapering surface narrowing towards a locating pin at the extremity thereof, the other having a locating socket into which the pin fits to couple said driven member to said connecting member.

* * * * *

UNITED STATES PATENT AND TRADEMARK OFFICE
CERTIFICATE OF CORRECTION

PATENT NO. : 5,617,601
DATED : April 8, 1997
INVENTOR(S) : Gregory J. McDougall

It is certified that error appears in the above-identified patent and that said Letters Patent is hereby corrected as shown below:

In column 6 at line 2 delete "form" and insert --from--

In column 7 at line 6 insert --the-- between "in" and "second"

Signed and Sealed this

Twenty-first Day of December, 1999

*Attest:*

Q. TODD DICKINSON

*Attesting Officer*  *Acting Commissioner of Patents and Trademarks*